(12) United States Patent
Reuther

(10) Patent No.: US 8,367,344 B2
(45) Date of Patent: Feb. 5, 2013

(54) METHOD OF DETECTING ONCOGENESIS OF HEMATOPOIETIC CELLS

(75) Inventor: Gary Willard Reuther, Tampa, FL (US)

(73) Assignee: University of South Florida, Tampa, FL (US)

(*) Notice: Subject to any disclaimer, the term of this patent is extended or adjusted under 35 U.S.C. 154(b) by 0 days.

(21) Appl. No.: 12/761,649

(22) Filed: Apr. 16, 2010

(65) Prior Publication Data

US 2010/0196915 A1 Aug. 5, 2010

Related U.S. Application Data

(63) Continuation of application No. PCT/US2008/080487, filed on Oct. 20, 2008.

(60) Provisional application No. 60/980,952, filed on Oct. 18, 2007.

(51) Int. Cl.
*G01N 33/48* (2006.01)
*G01N 33/53* (2006.01)
*G01N 33/574* (2006.01)
*C12N 5/07* (2010.01)
*C12N 15/00* (2006.01)

(52) U.S. Cl. ............... 435/6.14; 435/7.23; 435/7.92; 435/40.52; 435/374; 435/455; 436/64; 436/503

(58) Field of Classification Search ................ None
See application file for complete search history.

(56) References Cited

U.S. PATENT DOCUMENTS

2005/0214296 A1 9/2005 Kastelein et al.
2007/0111266 A1 5/2007 Sprecher et al.

FOREIGN PATENT DOCUMENTS

WO WO2005/079848 * 9/2005

OTHER PUBLICATIONS

Frappier et al, Journal of Biological Chemistry, 1989, vol. 264, pp. 334-341.*
The abstract of Pisetsky et al, Molecular Immunology, 1982, vol. 19, pp. 645-650.*
Koh et al (Oncogene, 2004, vol. 23, pp. 1214-1220).*
Real et al (Cancer Research, 1985, vol. 45, pp. 4401-4411).*
Pradhan et al (PNAS, published on-line Nov. 14, 2007, vol. 104, pp. 18502-18507).*
International Search Report PCT/US08/80487, dated Jul. 14, 2009.
Villarino et al., The IL-27R (WSX-1) Is Required to Suppress T Cell Hyperactivity During Infection, Immunity, 2003, vol. 19, pp. 645-655.
Lu et al., Expression of a Homodimeric Type 1 Cytokine Receptor is Required for JAK2V617F-Mediated Transformation, PNAS, 2005, vol. 102, No. 52, pp. 18962-18967.
Reuther et al., Identification and Characterization of an Activating TrkA Deletion Mutation in Acute Myeloid Leukemia, Molecular and Cellular Biology, 2000, vol. 20, No. 3, pp. 8655-8666.
Whitehead et al., Expression Cloning of lsc, a Novel Oncogene with Structural Similarities to the Dbl Family of Guanine Nucleotide Exchange Factors, The Journal of Biological Chemistry, 1996, vol. 271, No. 31, pp. 18643-18650.
Lucas et al., IL-27 Regulates IL-12 Responsiveness of Naive CD4+ T Cells Through Stat1-Dependent and—Independent Mechanisms, PNAS, 2003, vol. 100, No. 25, pp. 15047-15052.
Salcedo et al., IL-27 Mediates Complete Regression of Orthotopic Primary and Metastatic Murine Neuroblastoma Tumors: Role for CD8+ T Cells, The Journal of Immunology, 2004, vol. 173, pp. 7170-7182.
Afkarian et al., T-bet is a STAT 1-Induced Regulator of IL-12R Expression in Naive CD4+T Cells, Nature Immunology, 2002, vol. 3, No. 6, pp. 549-557.
Owaki et al., A Role for IL-27 in Early Regulation of Th1 Differentiation, The Journal of Immunology, 2005, vol. 175, pp. 2191-2200.
Pardanani et al., MPL515 Mutations in Myeloproliferative and Other Myeloid Disorders: A Study of 1182 Patients, Blood, 2006, vol. 108, No. 10, pp. 3472-3476.
Vainchenker et al., A Unique Activating Mutation in JAK2 (V617F) is at the Origin of Polycythemia Vera and Allows a New Classification of Myeloproliferative Diseases, Hematology, 2005, pp. 195-200.
Villarino et al., IL-27R Deficiency Delays the Onset of Colitis and Protects from Helminth-Induced Pathology in a Model of Chronic IBD, International Immunology, 2008, vol. 20, No. 6, pp. 739-752.
Molnar et al., Biosynthesis of Interleukin-6, an Autocrine Growth Factor for Melanoma, is Regulated by Melanoma-Derived Histamine, Cancer Biology, 2000, vol. 10, pp. 25-28.
Gilliland, Hematologic Malignancies, Current Opinion in Hematology, 2001, vol. 8, No. 4, pp. 189-191.
Nandurkar et al., The Human IL-11 Receptor Requires gp130 for Signalling: Demonstration by Molecular Cloning of the Receptor, Oncogene, 1996, vol. 12, pp. 585-593.
Nunez et al., Deregulated Bcl-2 Gene Expression Selectively Prolongs Survival of Growth Factor-Deprived Hemopoietic Cell Lines, The Journal of Immunology, 1990, vol. 144, No. 9, pp. 3602-3610.
Pflanz et al., IL-27, a Heterodimeric Cytokine Composed of EB13 and p28 Protein, Induces Proliferation of Naive CD4+T Cells, Immunity, 2002, vol. 16, pp. 779-790.
Pflanz et al., WSX-1 and Glycoprotein 130 Constitute a Signal-Transducing Receptor for IL-27, The Journal of Immunology, 2004, vol. 172, pp. 2225-2231.
Pikman et al., MPLW515L is a Novel Somatic Activating Mutation in Myelofibrosis with Myeloid Metaplasia, PLOS Medicine, 2006, vol. 3, No. 7, pp. 1140-1151.
Reuther et al., RasGRP4 Is a Novel Ras Activator Isolated from Acute Myeloid Leukemia, The Journal of Biological Chemistry, 2002, vol. 277, No. 34, pp. 30508-30514.

(Continued)

*Primary Examiner* — Karen Canella
(74) *Attorney, Agent, or Firm* — Michael L. Lawson; Robert J. Varkonyi; Smith & Hopen, P.A.

(57) ABSTRACT

Disclosed in a method of detecting cancer using IL-27 receptors. IL27R is a cytokine receptor identified as a novel oncogene from an acute myeloid leukemia patient. It induces cancer-like properties when expressed in cells and can activate a protein that causes various myeloid cell disorders. The data show cytokine receptors play unappreciated roles in mediating activation of signaling pathways in circulatory system cancers. Also method of screening for novel oncogenes using a functional, approach is disclosed using cytokine-dependent cells to screen for transforming events.

11 Claims, 9 Drawing Sheets

OTHER PUBLICATIONS

Sprecher et al., Cloning and Characterization of a Novel Class 1 Cytokine Receptor, Biochemical and Biophysical Research Communications, 1998, vol. 246, pp. 82-90.
Steensma et al., The JAK2 V617F Activating Tyrosine Kinase Mutation is an Infrequent Event in Both "Atypical" Myeloproliferative Disorders and Myelodysplastic Syndromes, Blood, 2005, vol. 106, No. 4, pp. 1207-1209.
Sternberg et al., The Role of Signal Transducer and Activator of Transcription Factors in Leukemogenesis, Journal of Clinical Oncology, 2004, vol. 22, No. 2, pp. 361-371.
Takeda et al., Cutting Edge: Role of IL-27/WSX-1 Signaling for Induction of T-Bet Through Activation of STAT1 During Initial Th1 Commitment, The Journal of Immunology, 2003, vol. 170, pp. 4886-4890.
Takeda et al., WSX-1 Over-Expression in CD4+ T Cells leads to Hyperproliferation and Cytokine Hyperproduction in Response to TCR Stimulation, International Immunology, 2005, vol. 17, No. 7, pp. 889-897.
Tanner et al., The Conserved Box 1 Motif of Cytokine Receptors Is Required for Association with JAK Kinases, The Journal of Biological Chemistry, 1995, vol. 270, No. 12, pp. 6523-6530.
Thompson et al., Photochemical Preparation of a Pyridone Containing Tetracycle: A Jak Protein Kinase Inhibitor, Bioorganic & Medicinal Chemistry Letters, 2002, vol. 12, pp. 1219-1223.
Towatari et al., Constitutive Activation of Mitogen-Activated Protein Kinase Pathway in Acute Leukemia Cells, Leukemia, 1997, vol. 11, pp. 479-484.
Villarino et al., Understanding the Pro- and Anti-Inflammatory Properties of IL-27, The Journal of Immunology, 2004, vol. 173, pp. 715-720.
Yamamoto et al., Activating Mutation of D835 Within the Activation Loop of FLT3 in Human Hematologic Malignancies, Blood, 2001, vol. 97, No. 8, pp. 2434-2439.
Artis et al., The IL-27 Receptor (WSX-1) Is an Inhibitor of Innate and Adaptive Elements of Type 2 Immunity, The Journal of Immunology, 2004, vol. 173, pp. 5626-5634.
Askew et al., Constitutive C-myc Expression in an IL-3-Dependent Myeloid Cell Line Suppresses Cell Cycle Arrest and Accelerates Apoptosis, Oncogene, 1991, vol. 6, pp. 1915-1922.
Baffy et al., Apoptosis Induced by Withdrawal of Interleukin-3 (IL-3) from an IL-3-Dependent Hematopoietic Cell Line is Associated with Repartitioning of Intracellular Calcium and Is Blocked by Enforced Bcl-2 Oncoprotein Production, The Journal of Biological Chemistry, 1993, vol. 268, No. 9, pp. 6511-6519.
Baxter et al., Acquired Mutation of the Tyrosine Kinase JAK2 in Human Myeloproliferative Disorders, The Lancet, 2005, vol. 365, pp. 1054-1061.
Carnicer et al., FLT3 Mutations are Associated with Other Molecular Lesions in AML, Leukemia Research, 2004, vol. 28, pp. 19-23.
Chen et al., Development of Th1-Type Immune Responses Requires the Type 1 Cytokine Receptor TCCR, Nature, 2000, vol. 407, pp. 916-920.
Deguchi et al., Cooperativity Between Mutations in Tyrosine Kinases and in Hematopoietic Transcription Factors in AML, Leukemia, 2002, vol. 16, pp. 740-744.
Frassanito et al., Autocrine Interleukin-6 Production and Highly Malignant Multiple Myeloma: Relation with Resistance to Drug-Induced Apoptosis, Blood, 2001, vol. 97, No. 2, pp. 483-489.
Frohling et al., Genetics of Myeloid Malignancies: Pathogenetic and Clinical Implications, Journal of Clinical Oncology, 2005, vol. 23, No. 26, pp. 6285-6295.
Gilliland et al., Focus on Acute Leukemias, Cancer Cell, 2002, vol. 1, pp. 417-420.
Gilliland, Molecular Genetics of Human Leukemias: New Insights Into Therapy, Seminars in Hematology, 2002, vol. 39, No. 4, Suppl. 3, pp. 6-11.
Greenberger et al., Demonstration of Permanent Factor-Dependent Multipotential (Erythroid/Neutrophil/Basophil) Hematopoietic Progenitor Cell Lines, Proc. Natl. Acad. Sci. USA, 1983, vol. 80, pp. 2931-2935.
Hunter, New IL-12-Family Members: IL-23 and IL-27, Cytokines with Divergent Functions, Nature Reviews/Immunology, 2005, vol. 5, pp. 521-531.
Ihle, Cytokine Receptor Signalling, Nature, 1995, vol. 377, pp. 591-594.
James et al., A Unique Clonal JAK2 Mutation Leading to Constitutive Signalling Causes Polycythaemia Vera, Nature, 2005, vol. 434, pp. 1144-1148.
Jones et al., Widespread Occurrence of the JAK2 V617F Mutation in Chronic Myeloproliferative Disorders, Blood, 2005, vol. 106, No. 6, pp. 2162-2168.
Kamiya et al., An Indispensable Role for STAT1 i IL-27-Induced T-bet Expression but Not Proliferation of Naive CD4+ T Cells, The Journal of Immunology, 2004, vol. 173, pp. 3871-3877.
Koh et al., Novel Retroviral Vectors to Facilitate Expression Screens in Mammalian Cells, Nucleic Acids Research, 2002, vol. 30, No. 24, pp. 1-7.
Kralovics et al., A Gain-of-Function Mutation of JAK2 in Myeloproliferative Disorders, The New England Journal of Medicine, 2005, vol. 352, No. 17, pp. 1779-1790.
Drahl. 2007. "Antibodies Against RNA Library Method to Generate Antibodies is Widely Applicable." Biochemistry. vol. 85. No. 52. p. 10.
Laneuville et al., Expression of the Chronic Myelogenous Leukemia-Associated p210bcr/abl Oncoprotein in a Murine IL-3 Dependent Myeloid Cell Line, Oncogene, 1991, vol. 6, pp. 275-282.
Larousserie et al., Differential Effects of IL-27 on Human B Cell Subsets, The Journal of Immunology, 2006, vol. 176, pp. 5890-5897.
Lee et al., The JAK2 V617F Mutation in De Novo Acute Myelogenous Leukemias, Oncogene, 2006, vol. 25, pp. 1434-1436.
Levine et al., The JAK2V617F Activating Mutation Occurs in Chronic Myelomonocytic Leukemia and Acute Myeloid Leukemia, but not in Acute Lymphoblastic Leukemia or Chronic Lymphocytic Leukemia, Blood, 2005, vol. 106, No. 10, pp. 3377-3379.
Levine et al., Activating Mutation in the Tyrosine Kinase JAK2 in Polycythemia Vera, Essential Thrombocythemia, and Myeloid Metaplasia with Myelofibrosis, Cancer Cell, 2005, vol. 7, pp. 387-397.
Lin et al., STAT Signaling in the Pathogenesis and Treatment of Leukemias, Oncogene, 2000, vol. 19, pp. 2496-2504.
Meyer et al., Remarkable Leukemogenic Potency and Quality of a Constitutively Active Neurotrophin Receptor, DeltaTrkA, Leukemia, 2007, vol. 21, pp. 2171-2180.
Saily et al., Signaling Through Interleukin-6 Receptor Supports Blast Cell Proliferation in Acute Myeloblastic Leukemia, Eur J Haematol, 1998, vol. 61, pp. 190-196.

* cited by examiner

SEQUENCE LISTING

```
<160> NUMBER OF SEQ ID NOS: 6

<210> SEQ ID NO 1
<211> LENGTH: 37
<212> TYPE: DNA
<213> ORGANISM: artificial sequence
<220> FEATURE:
<223> OTHER INFORMATION: Primer sequence to generate Box1 mutant IL-27R.

<400> SEQUENCE: 1
gtctgggaga aagttgctga tgctgccaac agcagtt                              37

<210> SEQ ID NO 2
<211> LENGTH: 37
<212> TYPE: DNA
<213> ORGANISM: artificial sequence
<220> FEATURE:
<223> OTHER INFORMATION: Primer sequence to generate Box1 mutant IL-27R.

<400> SEQUENCE: 2
aactgctgtt ggcagcatca gcaactttct cccagac                              37

<210> SEQ ID NO 3
<211> LENGTH: 24
<212> TYPE: DNA
<213> ORGANISM: artificial sequence
<220> FEATURE:
<223> OTHER INFORMATION: Forward PCR primer listed from 5' to 3'.

<400> SEQUENCE: 3 ctgcctctttt ctgaagccaa tggg                                           24
```

```
<210> SEQ ID NO 4
<211> LENGTH: 26
<212> TYPE: DNA
<213> ORGANISM: artificial sequence
<220> FEATURE:
<223> OTHER INFORMATION: Reverse PCR primer listed from 5' to 3'.

<400> SEQUENCE: 4
ctgaccatgt acaacgtatc actact                                        26

<210> SEQ ID NO 5
<211> LENGTH: 24
<212> TYPE: DNA
<213> ORGANISM: artificial sequence
<220> FEATURE:
<223> OTHER INFORMATION: Forward PCR primer listed from 5' to 3'.

<400> SEQUENCE: 5
gcacgttcat catcgagaag cagc                                          24

<210> SEQ ID NO 6
<211> LENGTH: 24
<212> TYPE: DNA
<213> ORGANISM: artificial sequence
<220> FEATURE:
<223> OTHER INFORMATION: Reverse PCR primer listed from 5' to 3'.

<400> SEQUENCE: 6
gcctgttgct tgttcacgaa accc                                          24
```

METHOD OF DETECTING ONCOGENESIS OF HEMATOPOIETIC CELLS

CROSS REFERENCE TO RELATED APPLICATIONS

This application is a continuation of prior filed International Application, Serial Number PCT/US2008/080487 filed Oct. 20, 2008, which claims priority to U.S. provisional patent application No. 60/980,952 filed Oct. 18, 2007 which is hereby incorporated by reference into this disclosure.

STATEMENT OF GOVERNMENT INTEREST

This invention was made with Government support under Grant No. CA098330 awarded by the National Cancer Institute. The Government has certain rights in the invention.

FIELD OF INVENTION

This invention relates to an medical diagnostic techniques and research cell lines. More specifically, the invention provides methods of testing for cancerous cells and methods of producing oncogenic research cell lines.

BACKGROUND OF THE INVENTION

Acute myeloid leukemia (AML) is a disease of the myeloid compartment of the hematopoietic system characterized by an accumulation of undifferentiated blast cells in the peripheral blood and bone marrow. AML is caused by multiple genetic and epigenetic changes that result in stimulation of mitogenic signals as well as deregulation of apoptosis and differentiation. It has been proposed that mutations in two different classes of oncogenes are required to induce AML. Mutations in class I oncogenes (e.g. Ras, Flt3) result in stimulation of proliferative and cell survival signals while mutations in class II oncogenes (e.g. AMLJ-Eto, PML-RARα) lead to inhibition of differentiation and subsequent cell death by apoptosis (Frohling S, et al., Genetics of Myeloid Malignancies: Pathogenetic and Clinical Implications, *J. Clin. Oncol.*, 2005 Sep. 10; 23(26):6285-95; Gilliland, D. G., Hematologic malignancies *Curr. Opin. Hematol.*, 2001 July; 8(4):189-91; Gilliland, D. G., Molecular genetics of human leukemias: New insights into therapy, *Semin. Hematol.*, 2002 October; 39(4 Suppl 3):6-11). While many mutations are recurrently found in AML patients, it is believed that additional mutations in AML exist and have yet to be identified (Gilliland, D. G., Tallman, M. S., Focus on acute leukemias, *Cancer Cell*, 2002 June; 1(5):417-20; Deguchi, K., Gilliland, D. G., Cooperativity between mutations in tyrosine kinases and in hematopoietic transcription factors in AML, *Leukemia*, 2002 April; 16(4):740-4; Carnicer, M. J., et al., FLT3 mutations are associated with other molecular lesions in AML, *Leuk. Res.*, 2004 January; 28(1): 19-23).

Screens have been performed to identify oncogenes in AML utilizing an efficient retroviral delivery, expression, and cDNA recovery system (Reuther, G. W., et al., RasGRP4 is a novel Ras activator isolated from acute myeloid leukemia, *J. Biol. Chem.*, 2002 Aug. 23; 277(34):30508-14; Reuther, G. W., et al., Identification and characterization of an activating TrkA deletion mutation in acute myeloid leukemia, *Mol. Cell Biol.*, 2000 December; 20(23):8655-66). Using this approach, a novel activating deletion mutation was identified in the TrkA tyrosine kinase in a patient with AML (Reuther, G. W., et al., *J. Biol. Chem.*, 2002 Aug. 23; 277(34):30508-14). This discovery provided the first evidence that TrkA may play a role in leukemogenesis. The deletion mutation identified has been shown to be leukemogenic in mice (Meyer J, et al., Remarkable leukemogenic potency and quality of a constitutively active neurotrophin receptor, [Delta]TrkA, *Leukemia*, 2007 October; 21(10):2171-80), further validating the approach to identify genes that contribute to leukemia formation.

Interleukin-27 (IL-27) was recently identified as a member of the IL-6/IL-12 family, and an important Th1 cytokine IL-27 is comprised of a helical subunit (p28) and a receptor-like protein related to IL12 p40, called Epstein-Barr induced gene 3 (EBI3). (Villarino, A. V., et al., IL-27R deficiency delays the onset of colitis and protects from helminth-induced pathology in a model of chromic IBD, *Int'l Immunol.*, 2008 June; 20(6):739-52; Owaki, T., et al., A role for IL-27 in early regulation of Th1 differentiation, *J. Immunol.*, 2005 Aug. 15; 175(4):2191-200) IL-27 binds to TCCR, a heterodimer of IL-27R, also called WSX-1, and gp130, which are restricted to lymphoid and myeloid cells (Villarino, A. V., et al., *Int'l Immunol.*, 2008 June; 20(6):739-52). Upon binding, IL-27 activates Jak1, -2, Stat1, -3, -4, -5, and TYK2, thereby inducing proliferation of naïve CD4+ cells, T-bet expression, and IL-12Rβ2 and IFN-γ expression (Lucas, S., et al., IL-27 regulates IL-12 responsiveness of naïve CD4+ T cells through Stat1-dependent and independent mechanisms, *Proc. Nat'l Acad. Sci.*, 2003 Dec. 9; 100(25):15047-52; Owaki, T., et al., 2005 Aug. 15; 175(4):2191-200).

Even with a large knowledge base about the causative genetics of AML, a more complete understanding of the molecular players is needed to identify targets for future therapeutic treatment for this disease.

SUMMARY OF THE INVENTION

Disclosed is a novel functional genetic screen to identify genes related to cancer cells and myeloid cell transformation, like AML formation. The identification of the ligand-binding component of the receptor for IL-27, IL-27R, was described as a novel transforming gene product. IL-27R is expressed on the cell surface of leukemic cells of AML patients and demonstrate that IL-27R can transform hematopoietic cells in a JAK-dependent manner. Also, IL-27R activates JAK2-V617F. Previously, only homodimeric type I cytokine receptors have been reported to activate this important JAK2 mutant. The data indicate that a single component of a heterodimeric cytokine receptor has the ability to aberrantly activate signaling pathways in hematopoietic cells. Thus, components of heterodimeric cytokine receptors play a role in myeloid diseases either through aberrant expression or activating mutations.

An aspect of the present invention is a method of detecting cancerous disorders utilizing a cell line or tumor of interest. The cell line or tumor of interest is contacted with an antibody which binds a biomarker for the cancerous disorder, specifically a component of interleukin 27 receptor, and the antibody is allowed to bind to the biomarker. The presence of the biomarker is then detected in the cell line or tumor. In some embodiments, the biomarker is a protein, mRNA, peptide, proteineaceous aggregate or derivative of a protein, mRNA, peptide, or proteineaceous aggregate. In further embodiments, the biomarker is WSX-1, a component of the receptor for IL-27.

The biomarker is detected using an immunoprotein assay which includes FACS, immunohistochemistry, and Western blot. However, other known immunoprotein assays are envisioned in this invention. In some embodiments the cell line or tumor of interest used herein is mammalian, and in more specific embodiments the cell line or tumor of interest is human. The cancerous disorder includes leukemia, myeloproliferative diseases, myeloid tumors, and acute myeloid leukemia. However, this method is useful for other cancerous diseases, and said diseases are also envisioned in this invention.

Also disclosed is a method of identifying cancerous genes using a functional genetic screen. A nucleic acid or nucleic acids are introduced into a retroviral delivery vector and the retroviral vector used to infect a cell culture of cytokine-dependent cells with the nucleic acid-retroviral vector. At least one cytokine is then removed from cell culture, where the at least one cytokine is required by the cytokine-dependent cells. The inserted nucleic acid or deritative thereof is isolated from surviving cells in the cell culture and identified. In some embodiments, the nucleic acid is cDNA. In certain embodiments, the screening method also involves isolating RNA from cells obtained from a patient, constructing cDNA from the RNA, and ligating the cDNA into the retroviral delivery vector. In specific embodiments, the cytokine dependent cells are 32D or BaF3 cells. However, this method is useful with other cytokine-dependent cells, which are also envisioned in this invention.

The screen is useful in screening for cancerous gene predictive of disorders such as leukemia, myeloproliferative diseases, myeloid tumors, and acute myeloid leukemia. However, this method is useful for other cancerous diseases, and said diseases are also envisioned in this invention. In certain embodiments, the nucleic acid is cDNA that encodes a heterodimeric transmembrane protein. Further embodiments provides that the cancerous gene is WSX-1.

The invention also provides a method of constructing a cancer research cell line. The cell line is constructed by isolating RNA from cells obtained from a patient and constructing cDNA from the RNA. The cDNA is then ligated into a retroviral vector and the cDNA introduced into a cell culture of cytokine-dependent cells. The cytokine is then removed from cell culture. In some embodiments, this produces a cell culture where the cDNA is stably transfected into the cells.

In certain embodiments, the cDNA encodes a heterodimeric transmembrane protein, and in more specific embodiments, the cDNA encodes WSX-1. The method further provides in some embodiments, introducing mutatant JAK2V617F into the cells. The method also provides, in certain embodiments, that the cytokine dependent cells are 32D or BaF3 cells. However, this method is useful with other cytokine-dependent cells, which are also envisioned in this invention.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
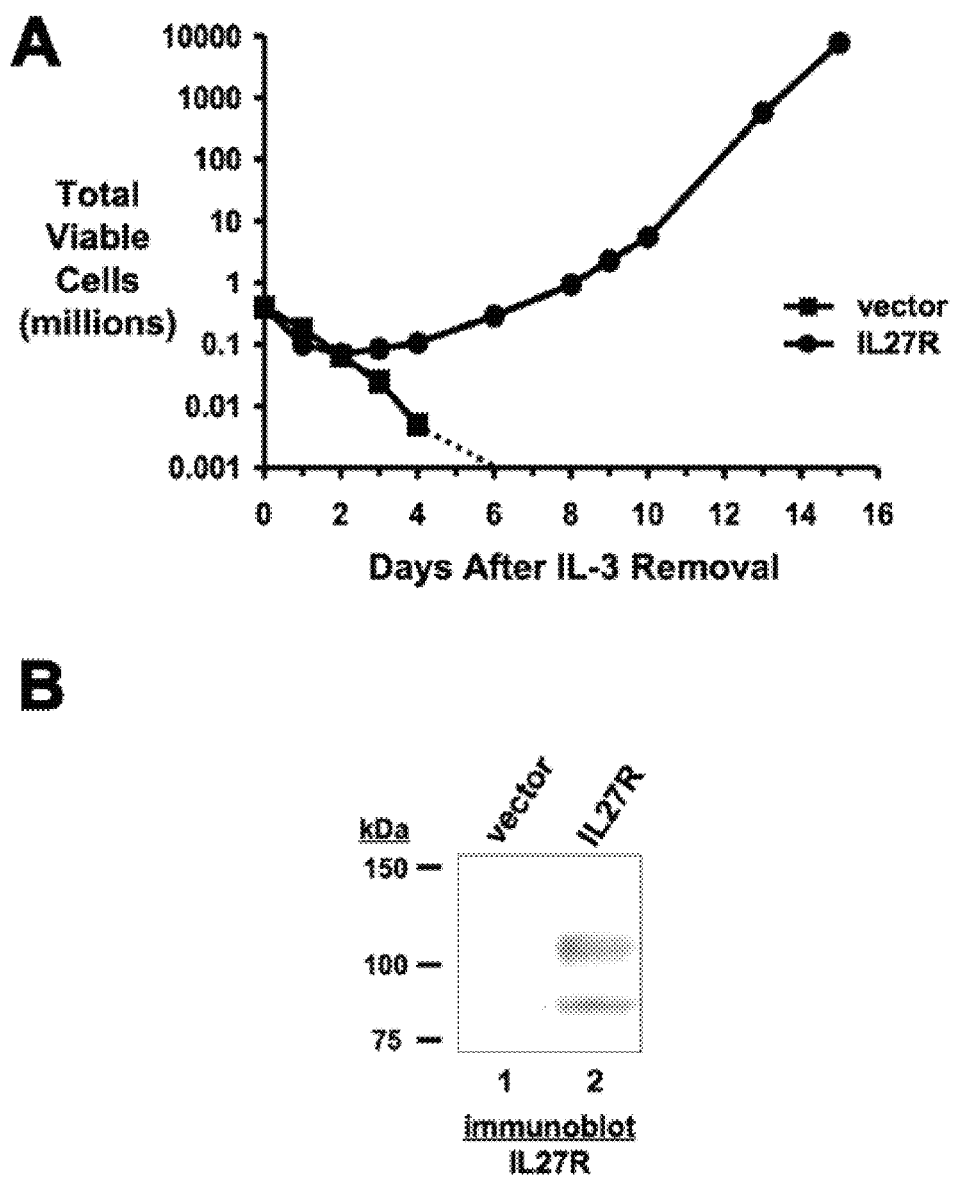
FIGS. 1(A) and (B) show IL-27R transformed 32D cells with IL-3-independence. (A) A graph of stably transfected cells were cultured in the absence of IL-3. The dotted line represents the total number of viable cells going below the limit of detection of a hemacytometer and to zero. (B) Cell lysates of 32D cells were immunoblotted for IL-27R. Cell lysates expressing a control vector (lane 1) or IL-27R (lane 2).

"Patient" is used to describe an animal, preferably a human, to whom treatment is administered, including prophylactic treatment with the compositions of the present invention.

Cell Culture and Retrovirus Production.

293T cells were maintained in DMEM supplemented with 10% fetal bovine serum (FBS). 32D cells and BaF3 cells were grown in RPMI supplemented with 10% FBS and 5% WEHI-3B conditioned medium as a source of IL-3. Ecotropic retrovirus was made in 293T cells using the pVPack system (Stratagene). Stable cell lines were generated by retroviral infection as described in the supporting information.

To stimulate cell cultures with IL-27, 32D and BaF3 cells expressing IL-27R were washed of growth factors and incubated in RPMI medium 1640 containing 0.1% BSA for 3 h. Cells were left untreated or stimulated with 100 ng/ml recombinant human IL-27 (R&D Systems) for 10 min. 293T cells were transfected with IL-27R, JAK2-V617F, and gp130 siRNA as indicated and as described. Two days later, cells were stimulated with 100 ng/ml human IL-27 for the length of time indicated and washed with ice-cold PBS, and cell lysates were prepared and analyzed by immunoblotting as described.

Construction of IL-27R Box 1 Mutant.

IL-27R Box1 mutant was generated by site-directed mutagenesis (Stratagene). See supporting information.

JAK2-V617F activation studies. 293T cells were transfected with combinations of pBabe-puro, pBabe-puro-IL-27RWT, or Box1mt, and MSCVneo-JAK2-WT or V617F (a gift of Ross Levine), and SMARTPool siRNA against gp130 (Dharmacon) or a non-silencing control siRNA (Qiagen) using calcium phosphate precipitation. Cells were lysed and analyzed by immunoblotting two days after transfection.

Production of Stable Cell Lines by Retroviral Infection. Stable cell lines were generated by retroviral infection using either the pBabepuro or pEYK3.1 retroviral vectors. For infections, $5\times10^5$ 32D or BaF3 cells were infected at 37° C. using 0.5-1 ml of retrovirus, 1-1.5 ml of growth medium, and 8 µg/ml polybrene (Sigma-Aldrich) in a final volume of 2 ml. Three hours later, cells were transferred into 100-mm-diameter dishes and growth medium was added to 10 ml. Two days later, cells were selected in puromycin 0.5 µg/ml (Sigma) or selected by IL-3 deprivation.

Construction of IL-27R Box 1 Mutant.

IL-27R Box 1 mutant was generated by site-directed mutagenesis (Stratagene). Primers used were: 5'-GTCTGG-GAGAAAGTTGCTGATGCTGCCAACAGCAGTT-3' and 5'-AACTGCTGTTGGCAGCATCAG-CAACTTTCTCCCAGAC-3'. Successful mutagenesis was confirmed by DNA sequencing followed by complete DNA sequencing of the entire IL-27R cDNA.

Neutralization of IL-27 with an Anti-IL-27 Antibody. Recombinant mouse IL-27 (eBioscience) (2.5 ng) was incubated in 100 µl of growth medium with 5 µg of goat anti-mouse IL-27 p28 antibody (AF1834) (R&D Systems) or 5 µg control goat IgG (Santa Cruz Biotechnology) at 37° C. for 1 h. These mixtures were then added to 293T cells expressing IL-27R to achieve final concentrations of 5 ng/ml IL-27 and 10 µg/ml antibody. These cells were then incubated at 37° C. for 5 or 10 min. Stimulation of cells was stopped by removing the medium and quickly adding ice-cold PBS. Cell lysis and immunoblotting were performed as described.

Treatment of IL-27R-Transformed Cells with Anti-IL-27 Neutralizing Antibodies. 32D and BaF3 cells transformed by IL-27R were plated at $0.5\times10^4$ cells per 100 µl of growth medium per well in a 96-well plate. A control volume of PBS or anti-mouse IL-27 neutralizing antibody (AF1834) (R&D Systems) was added to a final concentration of 10 µg/ml. Twenty-four and 48 h later, relative cell numbers were determined by adding 4 µl of CellTiter 96 Aqueous One Solution reagent (Promega) to each well. The plate was incubated for 2 h at 37° C. Absorbance was determined at 490 nm by using a 96-well plate reader. This was done in triplicate for each cell line at both 24 and 48 h after plating. In addition, cell viability was determined at 48 h by trypan blue exclusion.

cDNA Library Construction.

AML samples were obtained from the Moffitt Cancer Center Tissue Core Facility as viably frozen mononuclear cells from the bone marrow of untreated patients. Messenger RNA was isolated using FastTrack 2.0 mRNA Isolation Kit (Invitrogen). Double stranded cDNA was prepared using SuperScript Double Stranded cDNA Synthesis Kit (Invitrogen) and purified in two size fractions using the Geneclean III kit (Q-Biogene). cDNA fractions were ligated into the pEYK3.1 retroviral vector (Koh, E. Y., et al., Novel retroviral vectors to facilitate expression screens in mammalian cells., *Nucleic Acid Res.*, 2002 Dec. 15; 30(24):e142) and ligations were transformed into *E. coli* electrocompetent cells (Lucigen). The library contained approximately 3.3 million bacterial colonies with a cloning efficiency of about 90%.

Screening of cDNA Library and Isolation of cDNA from Cells.

32D cells expressing exogenous Bcl2 were infected with retrovirus made from the AML cDNA library. Four independent infections were done for each cDNA fraction. Two days after infection, cells were plated in the absence of IL-3 to select for IL-3-independent transformants. Genomic DNA was isolated from IL-3-independent cells and treated with Cre recombinase (NEB) to excise pEYK3.1 plasmids, containing putative transforming cDNAs, which were then isolated by bacterial transformation.

Cell Growth Analysis.

To assay 32D and BaF3 cell response to IL-3 deprivation, cells were washed twice with RPMI/10% FBS. Cells were plated at a concentration of $4\times10^5$/ml in RPMI/10% FBS and cell growth and viability were monitored by trypan blue exclusion.

Immunoblot Analyses.

Cells were washed in PBS and lysed in lysis buffer (25 mM Tris pH7.4, 150 mM NaCl, 25 mM NaF, 1% Triton-X100, 1 mM sodium vanadate, 2 mM sodium pyrophosphate, 10 µg/ml leupeptin, 2 µg/ml aprotinin, and 1 mM PMSF). Protein concentrations were determined by BCA protein assay kit (Pierce Biotechnology), and equal amounts of protein were analyzed by SDS-PAGE. Primary antibodies used in this study include: IL-27R (TCCR) (C-term) (Sigma), phospho-(P-) STAT1(Y701), P-STAT3(Y705), P-JAK1(Y1022/1023), P-JAK2(Y1007/1008), P-ERK(T202/Y204), JAK1, JAK2 (Cell Signaling Technology), P-STAT5(Y694) (BD Transduction Laboratories), STAT1, STAT3, STAT5, and ERK1 (Santa Cruz Biotechnology). Immunoblots were developed using ECL Western Blotting Substrate (Pierce Biotechnology).

Flow Cytometry for IL-27R Expression.

Expression of IL-27R was determined by flow cytometry using an anti-human TCCR/WSX-1 antibody (R&D Systems) labeled with Alexa Flour-647 (Invitrogen/Molecular Probes). Details provided in supporting information.

JAK Inhibitor I Studies.

32D cells were washed twice with RPMI containing 0.1% BSA and incubated in the same medium with either 0.1% DMSO, 0.5 µM or 2 µM JAK inhibitor I (EMD Biosciences/Calbiochem) for 3 hours before lysis. For cell growth and viability, cells were plated at a concentration of $2\times10^5$/ml in RPMI/10% FBS and either 0.1% DMSO or 0.5 µM JAK inhibitor I. Cell growth and viability were determined by trypan blue exclusion. After 24 hr of JAK inhibitor I treatment, the percentage of apoptotic cells and cell cycle profiles were determined by flow cytometry. See supporting information.

Flow Cytometry: IL-27R Expression.

Bone marrow cells were obtained as frozen mononuclear cells from the Moffitt Cancer Center Tissue Core under Institutional Review Board approval. Frozen bone marrow samples were thawed in RPMI medium 1640 containing 0.5% BSA. Fc receptors on $1\times10^6$ cells were blocked with purified mouse anti-human CD32 monoclonal antibody (BD PharMingen) in 50 µl RPMI medium 1640 containing 3% FBS at 4° C. for 15 min. Cells were washed with PBS and stained in 50 µl of RPMI medium 1640 containing 3% FBS, 10 µg/ml anti-human TCCR/WSX-1 antibody (AF1479) (R&D Systems) labeled with Alexa Fluor-647 (Invitrogen/Molecular Probes), and 1.25 µg/ml phycoerythrin-conjugated anti-human CD33 (eBioscience) for 1 h at 4° C. Cells were washed with PBS and resuspended in 300 µl of PBS with 0.1 µg/ml DAPI as a viability marker. Stained cells (at least 10,000 events) were analyzed on a LSR II with FACSDiva (BD Bioscience) and FlowJo software (Tree Star).

Flow Cytometry: Apoptosis and Cell Cycle Analysis. The percentage of apoptotic cells after 24 h JAK inhibitor I treatment was determined by flow cytometric analysis of annexin V-fluorescein (BD Biosciences) binding. Briefly, $1\times10^6$ cells were washed once with 1×PBS and resuspended in 100 µl of 1× binding buffer. The cells were transferred to 5-ml culture tubes and stained with 3 µl of annexin V-FITC and 8 µl of 10 µg/ml of propidium iodide (PI). The cells were incubated for 15 min at room temperature in the dark. Four-hundred microliters of 1× binding buffer was added to the samples and the cells were analyzed by flow cytometry. Flow cytometric analysis was performed on a FACS Scan instrument with CellQuest software (BD Biosciences) and data obtained were analyzed with FlowJo software (Tree Star). Cell cycle profiles after 24 h JAK inhibitor I treatment were determined by flow cytometric analysis of PI-stained cells. Briefly, $1\times10^6$ cells were washed once with 1×PBS and fixed and permeabilized with 70% ice-cold ethanol. Cells were stored at −20° C. for at least 24 h. The cells were washed once with 1×PBS and resuspended in 500 µl of PBS containing 0.1% Triton X-100, 0.2 µg/µl RNase A, and 20 µg/ml PI and incubated for 30 min at room temperature in the dark. Stained cells were then analyzed by flow cytometry using a FACS Scan with CellQuest software and analyzed with FlowJo software (Tree Star).

RT-PCR. RNA was extracted from $10\times10^6$ BaF3, 32D/IL-27R, and WEHI-3B cells by using a RNeasy mini kit (Qiagen). Reverse transcription was performed by using the SuperScipt III first strand synthesis system for RT-PCR (Invitrogen). The primers used for the PCR were mouse gp130: forward-5' CTG CCT CTT TCT GAA GCC AAT GGG 3' and reverse-5' GAC CAT GTA CAA CGT ATC ACT ACT 3' and mouse STAT 5: forward-5' GCA CGT TCA TCA TCG AGA AGC AGC 3' and reverse-5' GCC TGT TGC TTG TTC ACG AAA CCC 3'. These primers anneal to sequences derived from different exons of each gene. PCR conditions were 34 cycles of 94° C. denaturation for 30 s, 55° C. annealing for 30 s, and 72° C. extension for 1 min.

Cell Signaling Analyses in BaF3 Cells. BaF3 and 32D cells expressing a control vector (washed free of IL-3) or transformed by IL-27R were incubated in RPMI medium 1640 supplemented with 10% FBS and no cytokine for 4 h. Total cell lysates were prepared and analyzed by immunoblotting as described.

In Vitro Complex Formation of JAKs and IL-27R. GST-IL-27R fusion protein, containing the amino acids of the transmembrane and intracellular region of IL-27R, was generated by cloning the cDNA for amino acids 517-636 of IL-27Ra (NM_004843) into pGEX-2T. The fusion protein was induced and purified with glutathione Sepharose beads (Pierce Biotechnology) by standard procedures. Cell lysates from 32D cells and 293T cells transfected with empty vector (293T/vector), JAK2-WT (293T/JAK2-WT), or JAK2-V617F (293T/JAK2-VF) were diluted in incubation buffer [25 mM Tris (pH 7.4), 150 mM NaCl, 10% glycerol, and 0.1% Triton-X 100] containing 25 mM NaF, 1 mM sodium vanadate, 2 mM sodium pyrophosphate, 10 µg/ml leupeptin, 2 µg/ml aprotinin, and 1 mM PMSF). Lysates were rocked with GST-beads alone or beads containing GST fused to the transmembrane and intracellular region of IL-27R for 3 h at 4° C. Bound proteins were eluted with 2×SB and analyzed, along with total cell lysates, by immunoblotting with antibodies for JAK1, JAK2 (Cell Signaling Technologies), and actin (Sigma-Aldrich).

Functional Genetic Screens to Identify Myeloid Cell Oncogenes Uncover Novel Transforming Properties of IL-27R To identify oncogenes involved in AML and other myeloid disorders, functional genetic screens were developed in myeloid cells. 32D myeloid progenitor cells, which depend on IL-3 for growth and viability (Greenberger, J. S., et al., Demonstration of permanent factor-dependent multipotential (erythroid/neutrophil/basophil) hematopoietic progenitor cell lines, *Proc. Nat'l Acad. Sci. U.S.A.*, 1983 May; 80(10): 2931-5), were selected as the testing model. 32D/Bcl2 cells were selected for multiple reasons. First, removal of IL-3 leads to a very rapid apoptotic cell death of 32D cells and screens of parental 32D cells resulted in no cytokine independent isolates. Second, oncogenic expression in 32D cells needs to elicit an anti-apoptotic as well as a mitogenic signal to transform these cells to cytokine independence. Third, it is believed that transformation of myeloid cells in AML is caused by mutations that activate cooperating signaling pathways. When 32D cells are cultured in the absence of IL-3, they undergo cell cycle arrest and apoptosis (Askew, D. S., et al., Constitutive c-myc expression in an IL-3-dependent myeloid cell line suppresses cell cycle arrest and accelerates apoptosis, *Oncogene*, 1991 October; 6(10):1915-22).

32D cells have served as a model cell system to study the transforming properties of various leukemia-associated oncogenes, such as Bcr/Abl and Flt3, among others (Laneuville, P., et al., Expression of the chronic myelogenous leukemia-associated p210bcr/abl oncoprotein in a murine IL-3 dependent myeloid cell line, *Oncogene*, 1991 February; 6(2): 275-82; Yamamoto, Y., et al., Activating mutation of D835 within the activation loop of FLT3 in human hematologic malignancies, *Blood*, 2001 Apr. 15; 97(8):2434-9). In the current approach, cDNA was inserted into the model cells to represent the genes expressed in the leukemic cells of patients with AML. This cDNA was cloned into a retroviral vector (pEYK3.1, a gift of George Daley) designed for efficient delivery and proviral recovery (Koh, E. Y., et al., Novel retroviral vectors to facilitate expression screens in mammalian cells, *Nucleic Acids Res.*, 2002 Dec. 15; 30(24):e142). Retrovirus-containing cDNA libraries were created using AML patients and used this virus to infect 32D cells that exogenously express B-cell CLL/lymphoma 2 (Bcl2).

Culturing 32D cells without IL-3 resulted in cell death of the entire culture in a little over two days. However, expression of Bcl2 led to enhanced cell survival in the absence of IL-3 without inducing cell growth (data not shown). Two days after infection, 32D/Bcl2 cells were plated in medium lacking IL-3 to identify IL-3-independent transformants. Utilizing a cDNA library from an AML patient who exhibited AML of FAB subtype M5b, a monocytic leukemia with 93% blast cells and normal cytogenetics, cDNA was isolated representing a wildtype IL-27Ra (TCCR, WSX-1) (Sprecher, C. A., et al., Cloning and characterization of a novel class I cytokine receptor. *Biochem. Biophys. Res. Commun.*, 1998 May 8; 246(1):82-90) gene from multiple independent isolates of IL-3 independent cells. For simplicity, this gene and protein will be referred to as IL-27R.

Transformation of 32D Cells by IL-27R

Expression of IL-27R in 32D/Bcl2 cells is sufficient to transform these cells to IL-3 independence (data not shown). 32D cells were stably transfected with IL-27R or control vector and cultured in the absence of IL-3 starting on day 0. The total number of viable cells was determined by trypan blue exclusion. Interestingly, IL-27R also transforms parental 32D cells to IL-3 cytokine independence, seen in FIG. 1(A). Upon IL-27R transformation (circles) or a control vector (squares) cultured cells were grown in media without IL-3 starting on day 0. These results suggest that in the context of the expression of an entire library of cDNAs, expression of Bcl2 in 32D cells during the initial screen likely sensitized these cells to transformation to IL-3 independence. Cell lysates of the transfected cells lane 2 were immunoblotted with anti-IL-27R antibodies and analysis of the blot confirmed expression of IL-27R in these cells, seen in FIG. 1(B). The two protein bands of IL-27R are the result of glycosylation (data not shown). This is consistent with the presence of multiple glycosylation sites in the extracellular region of the receptor (Sprecher, C. A., et al., *Biochem. Biophys. Res. Commun.*, 1998 May 8; 246(1):82-90).

Figure 2:
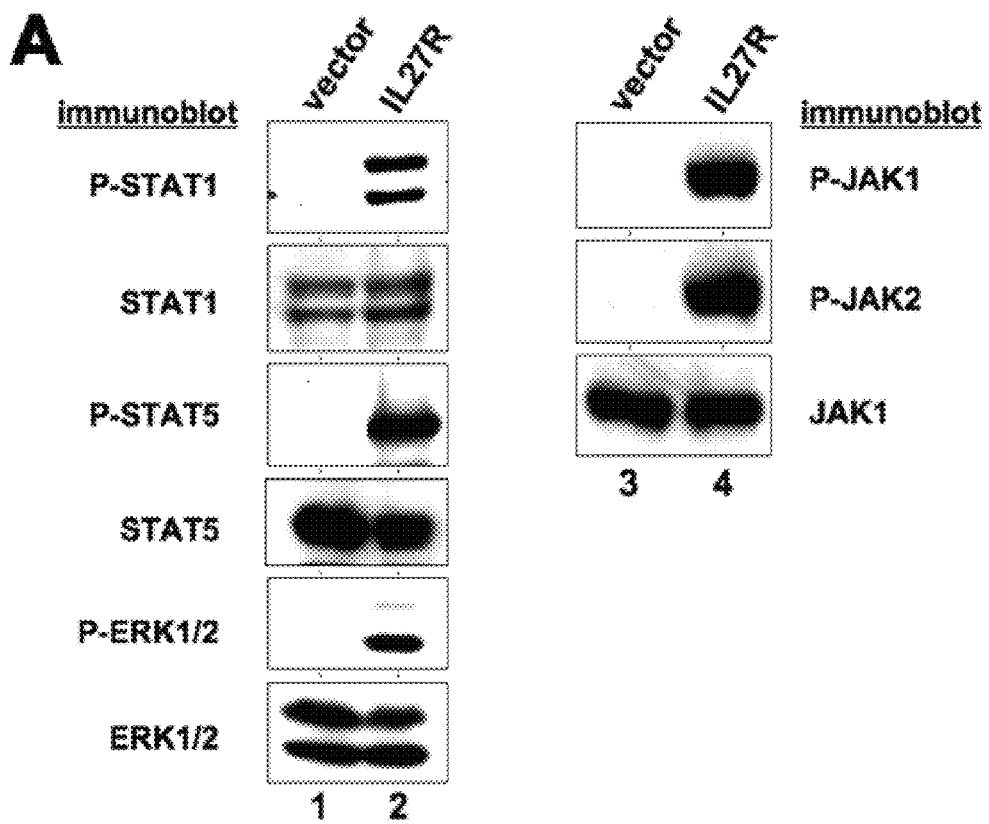
FIGS. 2(A) and (B) show IL-27R transformed 32D cells with IL-3-independence. (A) Cell lysates from an empty vector (lanes 1 and 3) or IL-27R (lanes 2 and 4) probed for STAT1, STAT5 and ERK 1/2. (B) Bone marrow mononuclear cells from normal and AML patients were analyzed for IL-27R.
Figure 2:
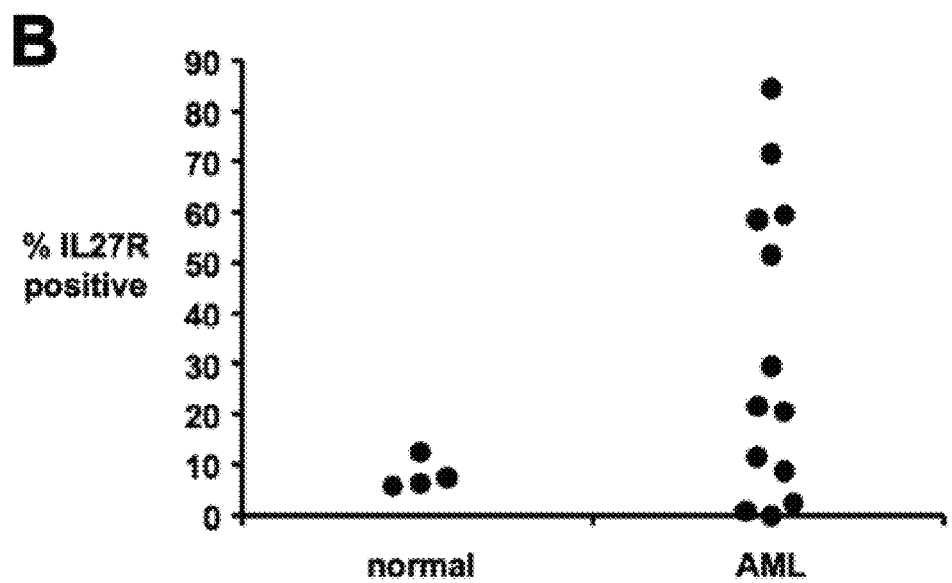
Figure 5:
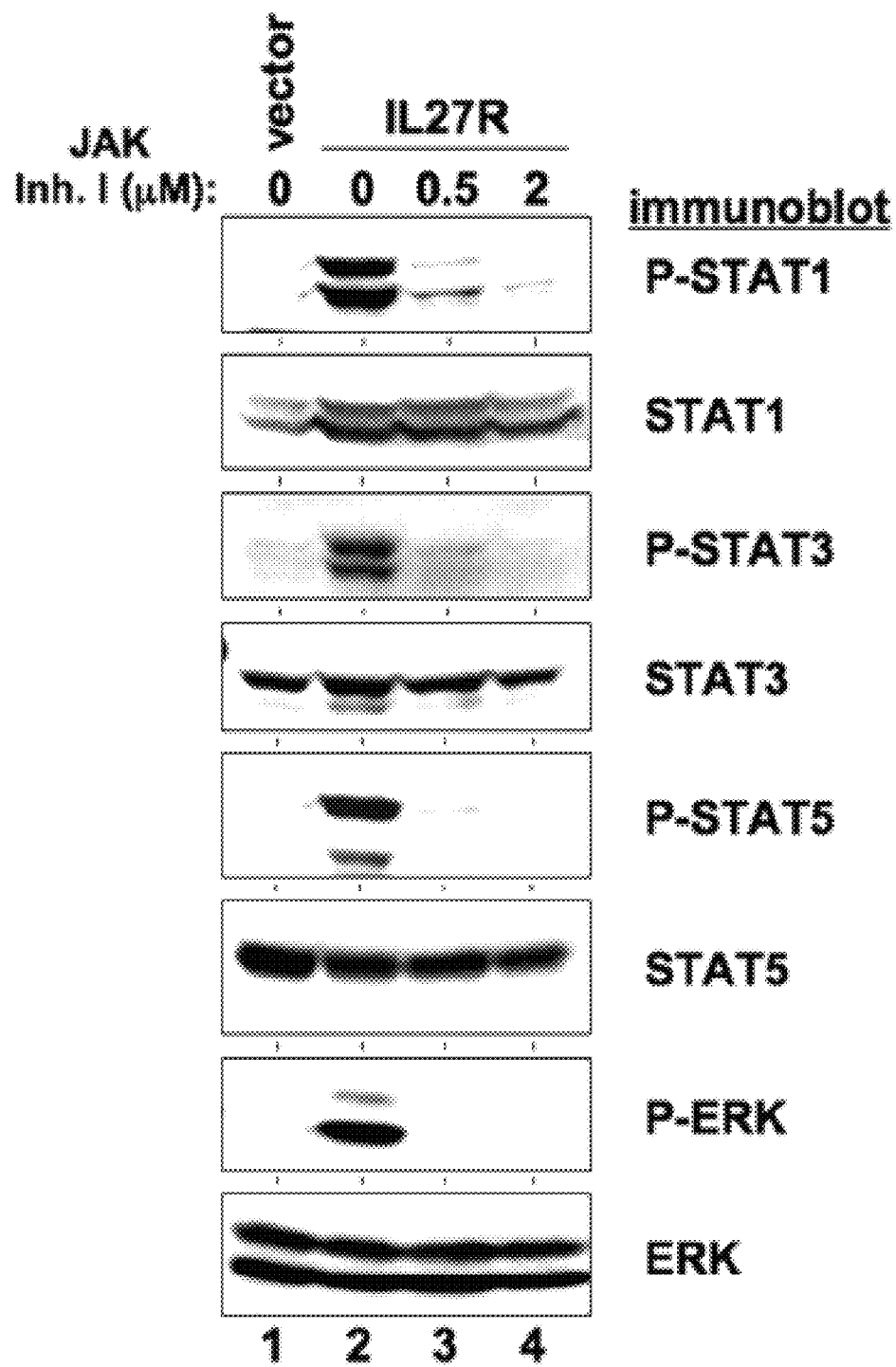
FIG. 5 shows transformation of 32D cells by IL-27R requires JAK family kinase activity. An immunoblot of IL-27R-transformed 32D cells, starved of serum/IL-3 blotted with antibodies that recognize STAT1, STAT5 and ERK 1/2.

IL-27R is a type I cytokine receptor that functions as the ligand-binding component of the receptor for IL-27 (Pflanz, S., et al., WSX-1 and glycoprotein 130 constitute a signal-transducing receptor for IL-27. *J. Immunol.*, 2004 Feb. 15; 172(4):2225-31; Pflanz, S., et al., IL-27, a heterodimeric cytokine composed of EBI3 and p28 protein, induces proliferation of naive CD4(+) T cells. *Immunity*, 2002 June; 16(6): 779-90). Signaling induced by IL-27 activates JAK and STAT proteins, including JAK1, -2, Tyk2, STAT1, -2, -3, -4, and -5 in various cell types (Kamiya, S., et al., An indispensable role for STAT1 in IL-27-induced T-bet expression but not proliferation of naive CD4+ T cells. *J. Immunol.*, 2004 Sep. 15; 173(6):3871-7; Lucas, S., et al., IL-27 regulates IL-12 responsiveness of naive CD4+ T cells through Stat1-dependent and -independent mechanisms. *Proc. Nat'l Acad. Sci. U.S.A.*, 2003 Dec. 9; 100(25):15047-52). There is clear evidence that JAK/STAT proteins are activated in myeloid disorders. STAT1, -3, and -5 are frequently activated by leukemogenic oncogenes and are activated in AML (Lin T S, et al., STAT signaling in the pathogenesis and treatment of leukemias. Oncogene, 2000 May 15; 19(21):2496-504; Sternberg, D. W. & Gilliland, D. G., The role of signal transducer and activator of transcription factors in leukemogenesis. *J. Clin. Oncol.*, 2004 Jan. 15; 22(2):361-71). JAK proteins, in particular JAK2, are mutationally activated in myeloproliferative disorders (Baxter, E. J., et al., Acquired mutation of the tyrosine kinase JAK2 in human myeloproliferative disorders. *Lancet*, 2005 March 19-25; 365(9464):1054-61; James, C., et al., A unique clonal JAK2 mutation leading to constitutive signalling causes polycythaemia vera. *Nature*, 2005 Apr. 28; 434(7037):1144-8; Kralovics, R., et al., A gain-of-function mutation of JAK2 in myeloproliferative disorders. *N. Engl. J. Med.*, 2005 Apr. 28; 352(17):1779-90; Levine, R. L., et al., Activating mutation in the tyrosine kinase JAK2 in polycythemia vera, essential thrombocythemia, and myeloid metaplasia with myelofibrosis. *Cancer Cell*, 2005 April; 7(4): 387-97; Jones, A. V., et al., Widespread occurrence of the JAK2 V617F mutation in chronic myeloproliferative disorders. *Blood*, 2005 Sep. 15; 106(6):2162-8) as well as a small fraction of AML (Lee, J. W., et al., The JAK2 V617F mutation in de novo acute myelogenous leukemias. *Oncogene*, 2006 Mar. 2; 25(9):1434-6; Levine, R. L., et al., The JAK2V617F activating mutation occurs in chronic myelomonocytic leukemia and acute myeloid leukemia, but not in acute lymphoblastic leukemia or chronic lymphocytic leukemia. *Blood*, 2005 Nov. 15; 106(10):3377-9). The activation state of these proteins was analyzed in 32D cells transformed by IL-27R (lanes 2 and 4) and determined that these cells have increased phosphorylated STAT1, STAT5, JAK1, and JAK2 compared to vector control cells, as seen in FIG. 2A. STAT3 is also activated in 32D cells transformed by IL-27R, seen in FIG. 5. Since transformation of 32D cells involves mitogenic signaling as well as inhibition of apoptosis, it was determined that ERK1/2 is activated in these cells, seen in FIG. 2A. These data indicate that IL-27R-mediated transformation of 32D cells is associated with activation of JAK/STAT and ERK pathways. In addition to STATs, ERKs are also commonly activated in AML cells (Towatari, M., et al., Constitutive activation of mitogen-activated protein kinase pathway in acute leukemia cells. *Leukemia*, 1997 April; 11(4):479-84). Thus, transformation by IL-27R results in activation of pathways which are frequently activated in AML. Activation of transforming signals by IL-27R is not associated with the autocrine production of factors that stimulate cell growth or survival (data not shown).

Figure 9:
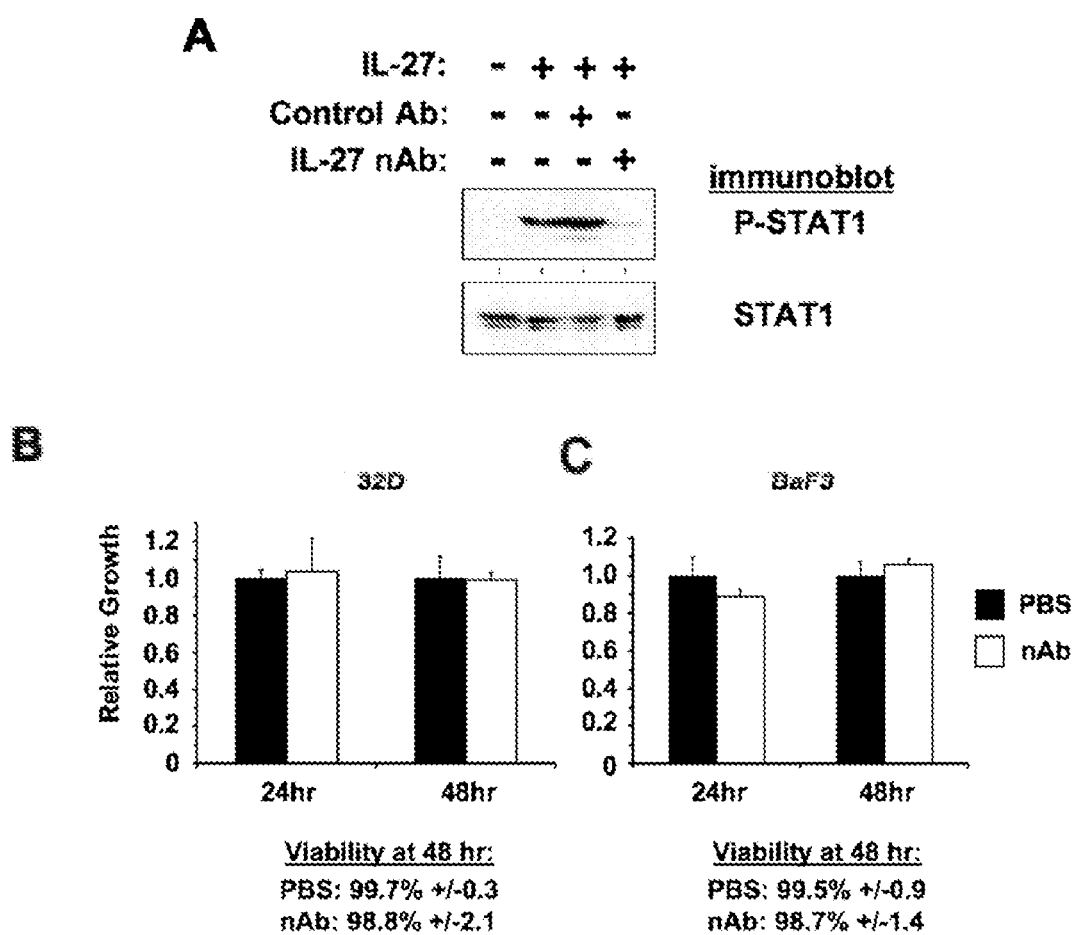
FIGS. 9(A), (B) and (C) show IL-27 neutralizing antibody does not affect the growth or viability of hematopoietic cells transformed by IL-27R. (A) IL-27 was incubated with control goat IgG antibody, a neutralizing polyclonal goat anti-IL-27 antibody (nAb), or a control volume of PBS and sued to stimulate IL-27R-expressing 293T cells. Cell lysates were prepared and analyzed by immunoblotting for P-STAT1 and total STAT as indicated. (B) 32D and (C) BaF3 cells transformed by IL-27R were cultured in the presence of neutralizing IL-27 antibody (nAb) or a control volume of PBS and cell growth measured by MTS assay t. Viability was determined at 48 h by trypan blue exclusion. The experiment was performed twice with each cell line and a representative experiment is shown. Error bars and ± indicate standard deviation of triplicate samples.

In addition, a neutralizing antibody to IL-27 did not affect the growth or viability of cells transformed by IL-27R, as seen in FIGS. 9(A), (B) and (C). IL-27 was incubated in complete growth medium with a control goat IgG antibody, a neutralizing polyclonal goat anti-IL-27 antibody (nAb), or a control volume of PBS for 1 h. These IL-27 samples were used to stimulate IL-27R-expressing 293T cells for 5 min at a final concentration of 2.5 ng/ml IL-27 and 10 mg/ml antibody. Cell lysates were prepared and analyzed by immunoblotting for P-STAT1 and total STAT. The nAb to IL-27 inhibited IL-27-mediated activation of STAT1. 32D and BaF3 cells were transformed by IL-27R and cultured in the presence of 10 mg/ml of the neutralizing IL-27 antibody (nAb) or a control volume of PBS. Cell growth was measured at 24 and 48 h by MTS assay and relative cell growth is shown normalized to the PBS control at each time point. Viability was determined at 48 h by trypan blue exclusion. The experiment was performed twice with each cell line and a representative experiment is shown. Error bars and ± indicate standard deviation of triplicate samples. The neutralizing IL-27 antibody does not affect cell growth or viability of IL-27R-transformed cells, suggesting an autocrine effect of IL-27 is not playing a role in IL-27R-mediated transformation.

Expression of IL-27R on the Cell Surface of AML Cells

Since IL-27R was identified as a transforming gene from the leukemic cells of an AML patient, this gene was analysed for common expression in AML patients. Bone marrow mononuclear cells were collected from normal and AML patients. Utilizing flow cytometry using an Alexa fluor-647-conjugated anti-IL-27R antibody, IL-27R was detected on the cell surface of AML cells (IL-27R-positive cells represented by a dot). Eight out of thirteen AML bone marrow samples tested had 2.5 to ten-fold greater number of cells expressing IL-27R (ranging from 0.33% to 84.6%) than the average observed in normal bone marrow cells (ranging from 6.3% to 12.8%), seen in FIG. 2(B) and data not shown. Mononuclear cells of bone marrow from normal and AML patients were stained with anti-IL-27R extracellular antibody conjugated to Alexa-fluor 647. Costaining was performed with CD33-PE and cells were analyzed on a LSRII (BD. Biosciences). This suggests IL-27R expression is retained in many AML patients. In all normal and AML samples tested, essentially all IL-27R-positive cells were CD33-positive, suggesting IL-27R is expressed in cells of the myeloid lineage in the bone marrow, data not shown.

IL-27R Requires JAK Activity to Transform Myeloid Cells

Figure 3:
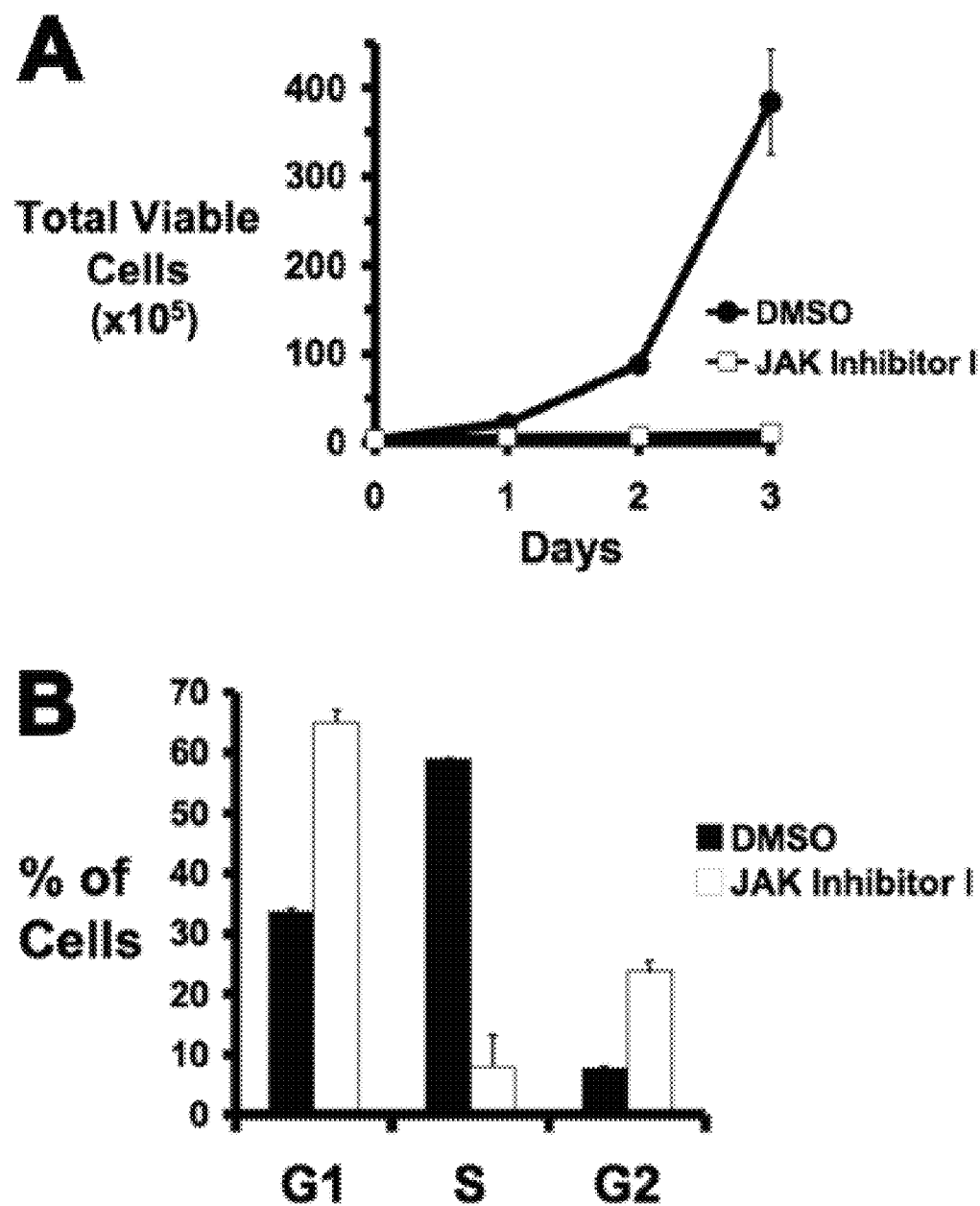
FIGS. 3(A) and (B) show transformation of 32D cells by IL-27R requires JAK family kinase activity. (A) Cell viability graph depicts 32D cells transformed with IL-27R were cultured in DMSO or JAK inhibitor. (B) After the JAK inhibitor I treatment, the DNA content present in each phase of the cell cycle was determined. Error bars indicate standard deviation of triplicate samples of a representative experiment.
Figure 4:
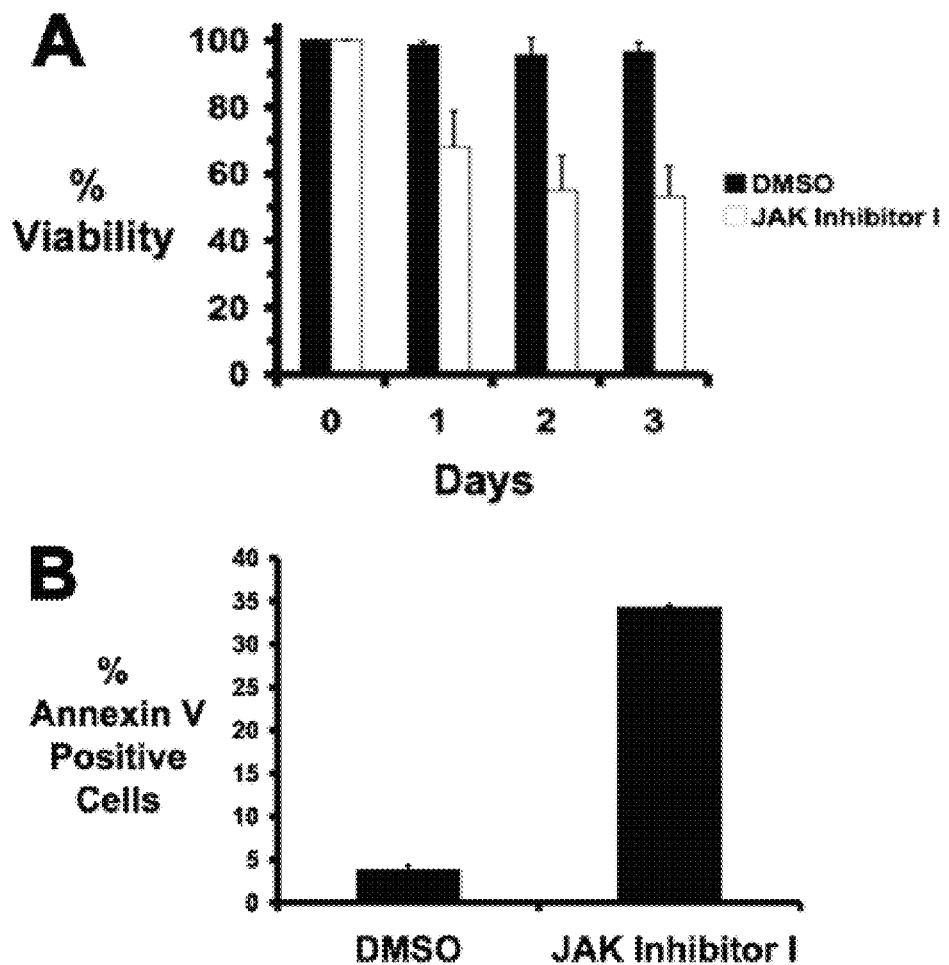
FIGS. 4(A) and (B) show transformation of 32D cells by IL-27R requires JAK family kinase activity. (A) Cell viability was determined by trypan blue exclusion. (B) After JAK inhibitor I treatment, apoptosis was determined and graphed using annexin V. Error bars indicate standard deviation of triplicates within a representative experiment.

The role of JAK family kinases in transformation by IL-27R was addressed by culturing 32D/IL-27R transformed cells with the pan-JAK inhibitor, JAK inhibitor I (Thompson, J. E., et al., Photochemical preparation of a pyridone containing tetracycle: a Jak protein kinase inhibitor. *Bioorg. Med. Chem. Lett.*, 2002 Apr. 22; 12(8):1219-23). Cells transformed with IL-27R were cultured in the presence of 0.1% DMSO or 0.5 µM JAK inhibitor I on day 0. The cells were subjected to a trypan blue viability assay, indicating that in the presence of JAK inhibitor I, the growth of these cells ceases, seen in FIG. 3(A). After 24 hr of JAK inhibitor I treatment, the DNA content present in each cell cycle stage was determined and plotted, showing JAK inhibitor I induces a G1 as well as a G2 cell cycle arrest and a dramatic decrease in the number of cells in S-phase after 24 hr of treatment, seen in FIG. 3(B). Cell viability, determined using trypan blue, also decreases in the presence of the inhibitor, seen in FIG. 4(A). This is due to the induction of apoptosis as determined by annexin V binding to the cells after 24 hr of treatment with inhibitor, as seen in FIG. 4(B). Transformed 32D cells were cultured in the presence of 0.1% DMSO (lane 2), 0.5 µM (lane 3) or 2 µM (lane 4) JAK inhibitor I. Control 32D cells starved of serum/IL-3 in the presence of 0.1% DMSO for three hr is shown in lane 1. Cell lysates were immunoblotted with antibodies that recognize STAT1, STAT3, STAT5, or ERK. JAK inhibitor I not only blocks STAT1, -3, and -5 phosphorylation induced by IL-27R, but it also prevents ERK1/2 activation, seen in FIG. 5. These experiments suggest the kinase activity of JAK family members is required for IL-27R-mediated cell growth and inhibition of apoptosis and that JAK activation is required for downstream activation of STATs and ERK1/2.

IL-27R Requires its Box 1 Motif to Transform 32D Cells

Figure 6:
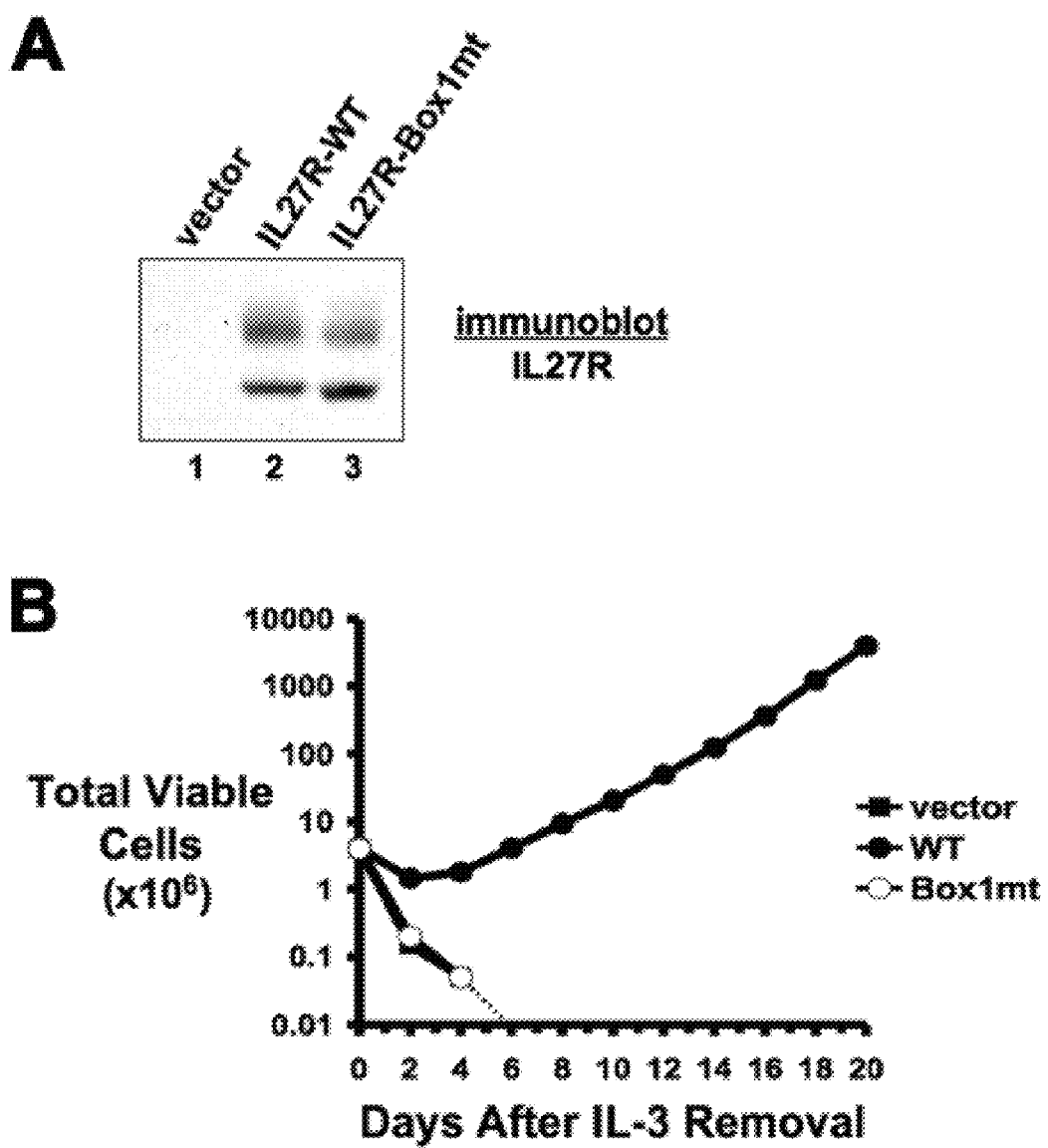
FIGS. 6(A) and (B) show 1'-27R requires a functional Box1 motif to transform 32D cells to cytokine independence. (A) A series of protein immunoblots of 32D cells infected with retrovirus after drug selection. (B) 32D cells were washed of IL-3 and cultured without IL-3 and the total number of viable cells was determined and graphed. The dotted line represents the total number of viable cells going below the limit of detection of a hemacytometer and to zero.

Within the cytoplasmic region of IL-27R is a Box 1 motif (Sprecher, C. A., et al., *Biochem. Biophys. Res. Commun.*, 1998 May 8; 246(1):82-90). This motif is often found in cytokine receptors and functions as an interaction motif with JAK proteins (Ihle, J. N., Cytokine receptor signalling. *Nature*, 1995 Oct. 19; 377(6550):591-4; Tanner, J. W., et al., The conserved box 1 motif of cytokine receptors is required for association with JAK kinases. J. Biol. Chem., 1995 Mar. 24; 270(12):6523-30). IL-27R has been shown to interact with JAK1 (Takeda, A., et al., Cutting edge: role of IL-27/WSX-1 signaling for induction of T-bet through activation of STAT1 during initial Th1 commitment. *J. Immunol.*, 2003 May 15; 170(10):4886-90), although JAK2 is also activated following IL-27 stimulation of cells (Kamiya, S., et al., *J. Immunol.*, 2004 Sep. 15; 173(6):3871-7). 32D cells were infected with retrovirus IL-27R or IL-27R containing a mutant Box 1 motif. The cells were treated for drug selection and cell lysates were immunoblotted for IL-27R expression. Mutation of conserved prolines in Box 1 motifs generates a motif that is severely impaired in its ability to bind to JAK proteins (Tanner, J. W., et al., *J. Biol. Chem.*, 1995 Mar. 24; 270(12):6523-30). Cells were infected with empty vector (lane 1), wildtype IL-27R (lane 2), or IL-27R containing a mutant Box 1 motif (lane 3), where residues were mutated within the IL-27R Box 1 motif to alanine, seen in FIG. 6(A). 32D cells stably expressing control vector (filled squares), wildtype IL-27R (WT) (filled circles), or IL-27R-Box1mt (Box1mt) (open circles) were cultured without IL-3. The total number of viable cells was determined at each time point by trypan blue exclusion. Removal of IL-3 from the growth medium of these cells results in complete cell death of the Box 1 mutant culture in a time course identical to cells expressing a control vector, seen in FIG. 6(B). Thus, IL-27R requires its Box 1 motif to transform myeloid cells. Collectively, the data suggest IL-27R-mediated transformation requires receptor-mediated activation of JAK family kinases.

IL-27R Transforms BaF3 Cells to Cytokine Independent Growth

Figure 7:
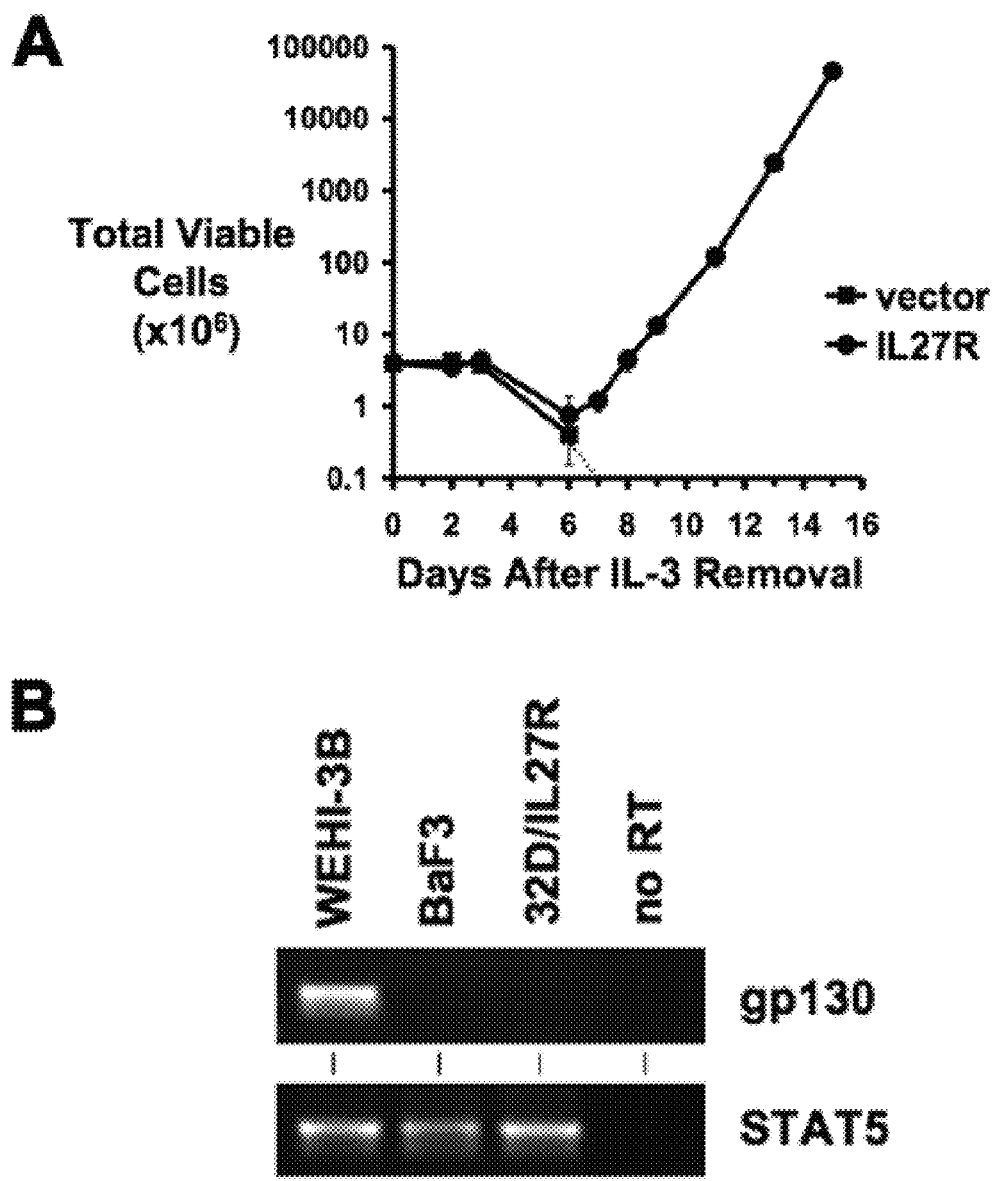
FIGS. 7(A) and (B) show IL-27R transforms IL-3-dependent BaF3 cells to cytokine independence. (A) A graph of the total number of viable IL-27R-infected (circles) or control vector-infected (squares) BaF3 cells without IL-3. The dashed line represents the total viable number of cells going below the limit of detection of a hemacytometer and to zero. (B) RT-PCR analysis for gp130 performed. WEHI-3B cells were used as a positive control, along with BaF3 cells, and 32D cells transformed by IL-27R. No reverse transcriptase (RT) is the negative control.

IL-27R requires the gp130 co-receptor to signal in response to IL-27 stimulation. BaF3 cells are IL-3-dependent pro-B cells that lack gp130 expression (Pflanz, S., et al., *J. Immunol.*, 2004 Feb. 15; 172(4):2225-31; Nandurkar, H. H., et al., The human IL-11 receptor requires gp130 for signalling: demonstration by molecular cloning of the receptor. *Oncogene*, 1996 Feb. 1; 12(3):585-93). Through gp130 reconstitution studies, these cells have been used to show the requirement for gp130 to induce cell signaling in response to IL-27 (Pflanz, S., et al., *J. Immunol.*, 2004 Feb. 15; 172(4):2225-31). To test if gp130 is required for IL-27R-mediated transformation of hematopoietic cells, BaF3 cells were infected with IL-27R-expressing vector and cultured in plated in RPMI/10% FBS in the absence of IL-3. Cell viability was determined using trypan blue. Like 32D cells, BaF3 cells are transformed to cytokine independence by IL-27R, seen in FIG. 7(A). This suggests that IL-27R does not require gp130 expression in order to elicit a transforming signal in cells. This also indicates that the transforming activity of IL-27R is not limited to 32D myeloid cells. RT-PCR for STAT5 served as a control for cDNA synthesis. RT-PCR analyses confirmed the lack of gp130 expression in BaF3 cells, seen in FIG. 7(B). Also, gp130 expression was not detected in 32D cells transformed by IL-27R suggesting that gp130 is not required for transformation of these cells and is not upregulated to facilitate IL-27R-mediated signaling during transformation, seen in FIG. 7(B). 32D and BaF3 cells expressing a control vector or transformed by IL-27R were incubated in the absence of cytokine Total cell lysates were prepared and analyzed by immunoblotting with antibodies that recognize the indicated proteins. Like 32D cells transformed by IL-27R, BaF3 cells transformed by IL-27R contain elevated levels of phosphorylated forms of JAK2, STAT5, STAT1, and ERK1/2. Phosphorylated STAT3 is also elevated in BaF3/IL-27R cells, but the lower levels of total STAT3 in these cells compared with 32D cells makes this less impressive. Analyses of signaling pathways in BaF3 cells transformed by IL-27R indicate similar JAK/STAT and ERK pathways are activated as in 32D cells transformed by IL-27R, data not shown.

Finally, while IL-27R-mediated transformation is gp130-independent, these observations still support the paradigm that IL-27-mediated signaling requires gp130 (Pflanz, S., et al., *J. Immunol.*, 2004 Feb. 15; 172(4):2225-31). 32D and BaF3 cells expressing IL-27R were washed of growth factors and incubated in RPMI medium 1640 containing 0.1% BSA for 3 h. Cells were left untreated or stimulated with 100 ng/ml IL-27 for 10 min and cell lysates analyzed by immunoblotting for phosphorylated (P-) and total STAT1. IL-27-induced signaling (as measured by STAT1 phosphorylation) is not observed in IL-27R-expressing 32D or BaF3 cells, which lack gp130, but is seen in IL-27R-expressing 293T cells, which express gp130, data not shown. 293T cells were transfected with IL-27R, JAK2-V617F, and gp130 siRNA as indicated. Two days later, cells were stimulated with 100 ng/ml IL-27 for the length of time indicated, and cell lysates were prepared and analyzed by immunoblotting for P-STAT1, total STAT1, and gp130. IL-27-induces activation of STAT1 in 293T cells that express IL-27R and gp130. This activation of STAT1 by IL-27 requires gp130, as gp130 depletion significantly impairs P-STAT1 formation. IL-27R/JAK2-V617F-mediated activation of STAT1 is not enhanced by IL-27. siRNA depletion of gp130 in 293T cells inhibits IL-27-induced phosphorylation of STAT1, data not shown.

IL-27R Activates JAK2-V617F

Figure 8:
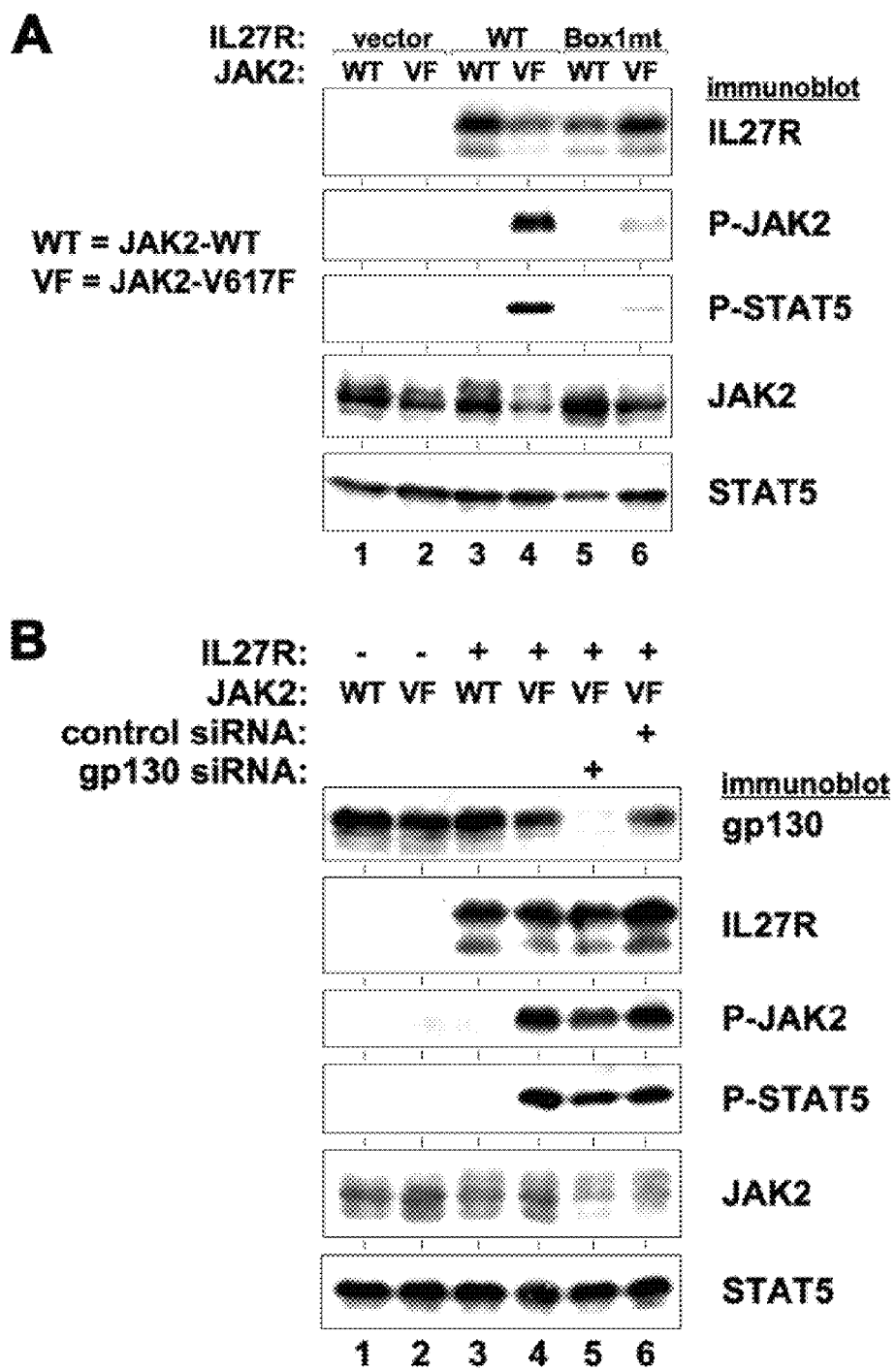
FIGS. 8(A) and (B) show activation of JAK2-V617F by IL-27R. (A) 293T cells cotransfected with IL-27R and JAK2 were immunoblotted. (B) The cells were then treated with siRNA (gp103), and lysates analyzed by immunoblot using JAK, STAT, and IL-27R antibodies. Control vector (lanes 1 and 2) and IL-27R (lanes 3 thru 6) along with JAK2 (WT, lanes 1 and 3), JAK2-V617F (VF, lanes 2, 4, 5, and 6), gp130 siRNA (lane 5), and control non-silencing siRNA (lane 6).

Homodimeric type I cytokine receptors have been shown to be required for the full activation of JAK2-V617F (Lu, X., et al., Expression of a homodimeric type I cytokine receptor is required for JAK2V617F-mediated transformation. *Proc. Nat'l Acad. Sci. U.S.A.* 2005 Dec. 27; 102(52):18962-7), a JAK2 mutant found in a variety of MPDs as well as AML (Steensma, D. P., et al., The JAK2 V617F activating tyrosine kinase mutation is an infrequent event in both "atypical" myeloproliferative disorders and myelodysplastic syndromes. *Blood,* 2005 Aug. 15; 106(4):1207-9). It is believed homodimeric cytokine receptors (e.g. EpoR) provide a scaffold upon which JAK2-V617F proteins can bind and become activated by transphosphorylation (Lu, X., et al., *Proc. Nat'l Acad. Sci. U.S.A.* 2005 Dec. 27; 102(52):18962-7). Such activation of mutant JAK2 is independent of ligand for the receptor. IL-27R is a type I cytokine receptor that normally functions as a heterodimeric partner with gp130 (Hunter CA New IL-12-family members: IL-23 and IL-27, cytokines with divergent functions. *Nat. Rev. Immunol.,* 2005 July; 5(7):521-31). However, the ability of IL-27R to transform BaF3 and 32D cells, which lack gp130 expression, suggests IL-27R does not require gp130 to transform cells. Seen in FIG. 8(A), 293T cells were transfected with control vector (lanes 1 and 2), IL-27R (WT, lanes 3 and 4), IL-27R-Box1mt (Box1mt, lanes 5 and 6), along with wildtype JAK2 (WT, lanes 1, 3, and 5) or JAK2-V617F (VF, lanes 2, 4, and 6). After transfection, cells lysates were analyzed by immunoblotting with antibodies against JAK, STAT, or IL-27R proteins. Since the transforming properties of IL-27R are not dependent on its heterodimeric partner gp130, IL-27R functions as homodimeric receptors and activates JAK2-V617F (Lu, X., et al., Proc. Nat'l Acad. Sci. U.S.A. 2005 Dec. 27; 102(52):18962-7), as well as its downstream target STAT5, in 293T cells, seen in FIG. 8(A). Expression of IL-27R along with wildtype JAK2 did not lead to activation of JAK2 or STAT5. IL-27R containing a mutated JAK-binding Box 1 motif, as in FIGS. 6(A) and (B) was impaired in activation of JAK2-V617F and STAT5 compared to wildtype IL-27R, seen in FIG. 8(A). Since 293T cells express gp130, activation of JAK2-V617F by IL-27R may require gp130. The transfected 293T cells were further transfected with gp130 siRNA. After transfection, cell lysates were analyzed by immunoblotting with antibodies that recognize JAK, STAT, gp130, or IL-27R. However, depletion of gp130 by siRNA had no effect on IL-27R-mediated activation of JAK2-V617F and STAT5 demonstrating this effect is gp130-independent, seen in FIG. 8(B). While the inventors could not co-immunoprecipitate IL-27R and JAK2 to demonstrate a presumed interaction, a complex formation between IL-27R and JAK2, as well as JAK1, was detected in vitro suggesting IL-27R may complex with JAK2 in cells. 32D cells and 293T cells were transfected with empty vector (293T/vector), JAK2-WT (293T/JAK2-WT), or JAK2-V617F (293T/JAK2-VF) and cell lysates incubated with beads containing GST alone or beads containing GST fused to the transmembrane and intracellular region of IL-27R. Bound proteins were eluted with 2×SB and analyzed along with total cell lysates by immunoblotting for JAK1, JAK2, and actin. JAK1 and JAK2 from each cell line complexed with GST-IL-27R but not GST alone. The V617F mutation does not alter the in vitro complex formation between JAK2 and IL-27R. Actin immunoblot indicates lack of nonspecific binding of an abundant cellular protein. Together, the data suggest that IL-27R functions in an analogous manner as homodimeric type I receptors to activate JAK2-V617F.

Discussion

Functional genetic screens of genes expressed in the leukemic cells of AML patients were utilized to identify genes that contribute to myeloid cell transformation. This approach uncovered novel cell transforming properties of IL-27R, the ligand-binding component of the receptor for IL-2. Importantly, IL-27R is frequently expressed on the cell surface of a greater number of bone marrow cells of AML patients than of cells of normal bone marrow, suggesting it plays a role in leukemogenesis.

IL-27R is a member of the IL-6/IL-12 receptor family (Villarino, A. V., et al., Understanding the pro- and anti-inflammatory properties of IL-27. *J. Immunol.,* 2004 Jul. 15; 173(2):715-20). A heterodimeric receptor complex of IL-27R/130 is required to activate signaling pathways in response to IL-27 stimulation of cells. This includes activation of JAK1, -2, Tyk2, STAT1, -2, -3, -4, and -5. IL-27 regulates various aspects of immune responses including T-cell-mediated immunity (Artis, D., et al., The IL-27 receptor (WSX-1) is an inhibitor of innate and adaptive elements of type 2 immunity. *J. Immunol.,* 2004 Nov. 1; 173(9):5626-34; Chen, Q., et al., Development of Th1-type immune responses requires the type I cytokine receptor TCCR. *Nature,* 2000 Oct. 19; 407(6806):916-20), and can also regulate the activity of B-cells, mast cells, and monocytes (Larousserie, F., et al., Differential effects of IL-27 on human B cell subsets. *J. Immunol.,* 2006 May 15; 176(10):5890-7). Interestingly, IL-6 can function as a growth factor for various cancer cells (Frassanito, M. A., et al., Autocrine interleukin-6 production and highly malignant multiple myeloma: relation with resistance to drug-induced apoptosis. *Blood,* 2001 Jan. 15; 97(2):483-9; Molnar, E. L., et al., Biosynthesis of interleukin-6, an autocrine growth factor for melanoma, is regulated by melanoma-derived histamine. Semin. Cancer Biol., 2000 February; 10(1):25-8), including AML blast cells (Saily, M., et al., Signaling through interleukin-6 receptor supports blast cell proliferation in acute myeloblastic leukemia. *Eur. J. Haematol.,* 1998 September; 61(3): 190-6), suggesting signaling by members of this cytokine receptor family can promote oncogenic cell growth. In support of this notion, Takeda (Takeda, A., et al., WSX-1 over-expression in CD4(+) T cells leads to hyperproliferation and cytokine hyperproduction in response to TCR stimulation. *Int'l Immunol.,* 2005 July; 17(7):889-97) have observed hyperproliferation of T-cells designed to over-express IL-27R.

This study shows that expression of IL-27R induces IL-3-independent growth of 32D myeloid and BaF3 pro-B cells (FIG. 1A). Since BaF3 cells lack gp130 expression, IL-27R-mediated transformation is not dependent on gp130. In addition, expression of gp130 could not be detected in 32D cells; demonstrating IL-27R does not require gp130 to elicit a transforming signal in myeloid cells. 32D cells transformed by IL-27R have constitutively activated JAK/STAT family members (FIG. 2A), the JAK-binding Box 1 motif of IL-27R is required for its transforming activity, and JAK inhibition blocks cell transformation by IL-27R. These data suggest IL-27R-mediated activation of JAK family members is critical for its transforming capacity.

JAK family proteins play a major role in myeloid disorders as highlighted by the discovery of the JAK2-V617F point mutation. JAK2-V617F likely contributes to the pathogenesis of various MPDs including polycythemia vera, essential thrombocytosis, and myelofibrosis. Homodimeric type I cytokine receptors have been shown to be required for JAK2-V617F-mediated activation and transformation. Homodimeric receptors including, EpoR, TpoR, and GCSFR support the activation of JAK2-V617F in a ligand-independent manner. These receptors likely provide a scaffold upon which mutant JAK2 proteins can interact, which is believed to be necessary for the activation of the mutant kinase. While IL-27R is a component of a heterodimeric cytokine receptor with gp130, it is capable of activating JAK2-V617F in cells in a gp130-independent manner (FIG. 3). This suggests IL-27R can functionally replace homodimeric cytokine receptors to support the activation of JAK2-V617F.

Recently, point mutations in Mpl, the gene for the type I cytokine receptor TpoR, have been found in JAK2-V617F-negative myelofibrosis and essential thrombocythemia patients (Pardanani, A. D., et al., MPL515 mutations in myeloproliferative and other myeloid disorders: a study of 1182 patients. (2006) *Blood*, 2006 Nov. 15; 108(10):3472-6; Pikman, Y., et al., MPLW515L is a novel somatic activating mutation in myelofibrosis with myeloid metaplasia. *PLoS Med.*, 2006 July; 3(7):e270). These mutations were identified under the hypothesis that patients who lack a JAK2 mutation may have other mutations that lead to JAK2 activation, such as mutations in upstream activators of JAK2 including cytokine receptors. The identification of point mutations in Mpl in myeloid disorders suggests mutations in other type I cytokine receptors may also contribute to diseases of the myeloid system. The data suggests that contribution of heterodimeric cytokine receptors to JAK2-V617F pathogenesis, as well as JAK2-V617F-negative myeloid disorders, should be considered.

This data is the first to suggest a non-mutated single chain of a heterodimeric type I cytokine receptor has the ability to transform hematopoietic cells. The data further shows that a single component of a heterodimeric type I cytokine receptor can functionally replace a homodimeric type I receptor as an activator of JAK2-V617F. In light of this, the data shows heterodimeric type I cytokine receptors play unappreciated roles in mediating activation of signaling pathways in myeloid disorders and, like TpoR, such receptors contribute to JAK2-V617F-negative MPDs. This contribution occurs through altered expression or mutation of the receptor, as seen in patients with MPDs as well as AML.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a wireless test device, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of detecting leukemia, myeloproliferative diseases, myeloid tumors, and acute myeloid leukemia comprising the steps of:
providing a hematopoietic cell line or a sample comprising hematopoietic cells;
contacting the hematopoietic cell line or a sample comprising hematopoietic cells with an antibody which binds a biomarker for the cancerous disorders, wherein the biomarker is related to a component of interleukin 27 receptor;
allowing the biomarker to bind to the antibody; and
detecting the presence of the biomarker in said cell line or said sample using an immunoprotein assay;
wherein the presence of the biomarker is indicative of leukemia, myeloproliferative diseases, myeloid tumors, and acute myeloid leukemia.

2. The method of claim 1, wherein the biomarker is selected from the group consisting of protein, peptide, or proteineaceous aggregate.

3. The method of claim 2, wherein the biomarker is WSX-1.

4. The method of claim 1, wherein the immunoprotein assay is selected from the group consisting of FACS, immunohistochemistry, and Western blot.

5. The method of claim 1 wherein the hematopoietic cell line or a sample comprising hematopoietic cells is mammalian.

6. The method of claim 5 wherein the hematopoietic cell line or a sample comprising hematopoietic cells is human.

7. A method of constructing a cancer research cell line, comprising the steps of
isolating RNA from cells obtained from a patient;
constructing cDNA from the RNA, wherein the cDNA encodes a heterodimeric transmembrane receptor protein for IL-27;
ligating the cDNA into a retroviral vector;
introducing the cDNA into a IL-27 dependent cell culture; and
removing an IL-27 cytokine from cell culture.

8. The method of claim 7, wherein the gene introduced into the cell culture is a stably transfected into the cells.

9. The method of claim 7, wherein the cDNA encodes WSX-1.

10. The method of claim 7, wherein the cytokine dependent cells are selected from the group consisting of 32D and BaF3.

11. The method of claim 7, further comprising introducing mutant JAK2V617F into the cells.

* * * * *